United States Patent [19]

Beck et al.

[11] Patent Number: 4,788,208

[45] Date of Patent: Nov. 29, 1988

[54] 2,4-DICHLOROTHIAZOLE DERIVATIVES AND PROCESSES FOR THEIR PREPARATION

[75] Inventors: Gunther Beck, Leverkusen; Rüdiger Schubert, Bergisch-Gladbach, both of Fed. Rep. of Germany

[73] Assignee: Bayer Aktiengesellschaft, Leverkusen, Fed. Rep. of Germany

[21] Appl. No.: 150,364

[22] Filed: Jan. 29, 1988

Related U.S. Application Data

[63] Continuation of Ser. No. 826,470, Feb. 5, 1986, abandoned.

[30] Foreign Application Priority Data

Feb. 21, 1985 [DE] Fed. Rep. of Germany ....... 3505900

[51] Int. Cl.$^4$ .................... C07D 277/32; A01N 43/78
[52] U.S. Cl. ..................................... 514/365; 548/202
[58] Field of Search .................. 548/202; 514/365

[56] References Cited

U.S. PATENT DOCUMENTS

| | | | |
|---|---|---|---|
| 3,833,601 | 9/1974 | Beck et al. | 548/202 |
| 4,555,577 | 11/1985 | Beck et al. | 548/200 |
| 4,645,525 | 2/1987 | Forster et al. | 71/88 |

FOREIGN PATENT DOCUMENTS

| | | | |
|---|---|---|---|
| 0053765 | 6/1982 | European Pat. Off. | 548/202 |
| 0115811 | 8/1984 | European Pat. Off. | 548/202 |
| 2213865 | 10/1973 | Fed. Rep. of Germany | 548/202 |
| 2844270 | 10/1978 | Fed. Rep. of Germany | 548/202 |

*Primary Examiner*—Robert Gerstl
*Attorney, Agent, or Firm*—Sprung Horn Kramer & Woods

[57] ABSTRACT

The present invention relates to novel 2,4-dichlorothiazole derivatives of the formula

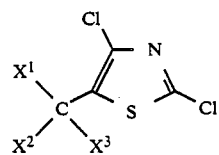

wherein $X^1$, $X^2$ and $X^3$ may be H or chlorine. These compounds are useful as starting materials for highly active herbicides and also themselves useful as fungicides. Processes for the preparation of these compounds are also disclosed.

4 Claims, No Drawings

2,4-DICHLOROTHIAZOLE DERIVATIVES AND PROCESSES FOR THEIR PREPARATION

This is a continuation of application Ser. No. 826,470, filed Feb. 5, 1986, now abandoned.

The present invention relates to new 2,4-dichlorothiazole derivatives and several processes for their preparation.

New 2,4-dichlorothiazole derivatives of the formula $$\text{(I)}$$

in which
X$^1$ represents hydrogen or chlorine,
X$^2$ represents hydrogen or chlorine and
X$^3$ represents hydrogen or chlorine,
have been found.

Specifically, the following compounds have been found (Ia), (Ib), (Ic), (Id)

It has furthermore been found that the 2,4-dichlorothiazole derivatives of the formula (I) are obtained by a process in which (a) 5-methyl-2,4-thiazolidinedione of the formula $$\text{(II)}$$

is reacted with at least 2 moles of phosphorus oxychloride (POCl$_3$) in the presence of catalytic amounts of N-alkylsubstituted carboxylic acid amides, or in which (b) ($\alpha$) 2,4-dichloro-5-methylthiazole of the formula (Ia), ($\beta$) 2,4-dichloro-5-chloromethylthiazole of the formula (Ib) or ($\gamma$) 2,4-dichloro-5-dichloromethylthianole of the formula (Ic)

is reacted with chlorine at elevated temperature, with exposure to light.

Formula (I) and formulae (Ia) to (Id) provide definitions of the 2,4-dichlorothiazole derivatives according to the invention.

If 2 moles of phosphorus oxychloride are used per mole of 5-methyl-2,4-thiazolidinedione in process (a) according to the invention, the course of the reaction can be represented by the following equation:

If 2,4-dichloro-5-methylthiazole is used as the starting substance in process (b)/variant ($\alpha$) according to the invention, the course of the reaction with chlorine can be represented by the following equations, depending on the degree of chlorination:

If 2,4-dichloro-5-chloromethylthiazole is used as the starting substance in process (b)/variant ($\beta$) according to the invention, the course of the reaction with chlorine can be represented by the following equations, depending on the degree of chlorination:

If 2,4-dichloro-5-(dichloromethyl)-thiazole is used as the starting substance in process (b)/variant ($\gamma$) according to the invention, the course of the reaction with chlorine can be represented by the following equation:

The 5-methyl-2,4-thiazolidinedione required as a starting substance in process (a) according to the invention is known.

In carrying out process (a) according to the invention, 2 moles of phosphorus oxychloride are required for complete conversion of the starting compound. However, to achieve a better yield, an excess of phosphorus oxychloride, which can be up to five times the stoichiometrically required amount, is in general employed, this compound simultaneously serving as the solvent or as the reaction medium. The reaction is preferably carried out with 3 to 8 moles of phosphorus oxychloride per mole of 5-methyl-2,4-thiazolidinedione.

N-Alkyl-substituted carboxylic acid amides which may be mentioned are: dimethylformamide, N,N-dimethylacetamide, 1-methyl-2-pyrrolidinone and tetramethylurea. The reaction is preferably carried out with dimethylformamide. In general, the N-alkyl-substituted carboxylic acid amides are employed in amounts of between 0.1 and 10 mol %, based on 1 mole of 5-methyl-2,4-thiazolidinedione. The reaction is preferably carried out with amounts of between 1 and 5 mol %.

The reaction temperatures are in general between about 50° C. and the boiling point of the reaction mixture (about 105° C.) The reaction is preferably carried out at the reflux temperature of the reaction mixture (100°–110° C.) to achieve the fastest possible reaction.

The mixture is heated until the evolution of HCl gas has virtually ended. If the reaction is carried out at the reflux temperature of the reaction mixture, the reaction has in general ended after 5 to 10 hours.

The reaction mixture can be worked up and the 2,4-dichloro-5-methylthiazole isolated in the pure form in the customary manner in two different ways: the reaction mixture is either introduced into excess water and, after hydrolysis of the excess phosphorus oxychloride, the 2,4-dichloro-5-methylthiazole is extracted with an organic water-immiscible solvent, for example methylene chloride, and the organic phase is then subjected to fractional distillation, or both the excess phosphorus oxychloride and the 2,4-dichloro-5-methylthiazole are distilled off from the reaction mixture, the two compounds being separated by fractional distillation at the same time or thereafter. Mixed forms of the two working-up routes described can of course also be used.

The 2,4-dichloro-5-methylthiazole required in carrying out variant (α) of process (b) according to the invention was not hitherto known. However, it can be prepared by process (a) according to the invention.

In carrying out variant (α) of process (b) according to the invention, 2,4-dichloro-5-methylthiazole is reacted with chlorine at elevated temperature with exposure to light. The reaction is in general carried out in the temperature range between 50° C. and 250° C. It can be carried out with or without a diluent. Possible diluents are all the solvents which are inert under the reaction conditions. Solvents which may be mentioned are perchlorinated organic hydrocarbons, such as carbon tetrachloride, hexachlorobutadiene and octachlorocyclopentene, or inorganic acid chlorides, such as phosphorus oxychloride.

In carrying out variant (α) of process (b) according to the invention, two different paths can be taken in respect of the chlorination technique: the first path ($b_1$) is of lower selectivity and thus in general requires subsequent fractional distillation to prepare the chlorination products (Ib), (Ic) and (Id) in a pure form. The second path ($b_2$) is of higher selectivity and in general gives the chlorination products mentioned, in particular 5-chloromethyl-2,4-dichlorothiazole (Ib), with only small concomitant amounts of products with a higher degree of chlorination.

In detail, process ($b_1$) is carried out by a procedure in which chlorine gas is passed into a liquid phase consisting of 2,4-dichloro-5-methylthiazole and, if appropriate, one of the abovementioned chlorination-resistant diluents in the temperature range between 50° and 250° C., with exposure to light. The reaction is in general carried out with 1 to 10 ml of diluent per gram of 2,4-dichloro-5-methylthiazole. The customary UV lamps are in general used as the source of light, and irradiation can be effected both externally and internally (immersion lamp). However, if the preparation of a chlorination mixture is desired, in which the compound with the lowest degree of chlorination, 5-chloromethyl-2,4-dichlorothiazole, predominates, a source of light with a lower radiation energy, for example a neon tube (fume cupboard illumination) may be advantageous.

The amount of chlorine to be used depends on the one hand on which chlorination product is required as the main product; higher amounts of chlorine of course effect a higher degree of chlorination of the reaction mixture. On the other hand, the amount of chlorine to be used depends greatly on the other reaction conditions, in particular temperature, light source and dimensions of the apparatus. The reaction is in general carried out with amounts of chlorine of between 1 and 15 moles of chlorine per mole of 2,4-dichloro-5-methylthiazole The reaction times depend on the one hand greatly on the reaction temperature, and on the other hand on the required degree of chlorination of the reaction mixture and on the batch size. They are therefore in general between 0.5 and 100 hours.

Since the boiling points of 5-chloromethyl-2,4-dichlorothiazole (Ib) (boiling point: 118° to 119° C./20 mbar) and of 2,4-dichloro-5-(dichloromethyl)-thiazole (Ic) (boiling point: 120° to 121° C./20 mbar) are close to one another, it is advisable, for preparation of one of the two compounds in the pure form, to control the chlorination by monitoring by gas chromatography so that, in the case of preparation of (Ib) in the pure form, compound (Ic) is not yet formed or is formed only to a small degree, whilst in the case of preparation of (Ic) in the pure form, compound (Ib) is no longer present.

In the case of preparation of the compound (Id), it may be advantageous, to avoid formation of undesirable byproducts with a higher chlorine content, to interrupt the chlorination reaction when the content of (Id), determined by gas chromatography, is 50 to 75% and to separate the mixture of (Ic) and (Id) by fractional distillation.

A suitable device for fractional distillation of, for example, a mixture of (Ic) and (Id) consists of, for example, a packed column which has a mirrored vacuum jacket and an effective length of 1 m, is filled with Wilson glass spirals 3 to 4 mm in diameter and is equipped with a column head with a magnetic vapour separator (reflux ratio, for example, 80:2).

The chlorination process ($b_2$) of higher selectivity which is suitable at least for the preparation of 5-chloromethyl-2,4-dichlorothiazole (Ib) is described in principle in German Offenlegungsschrift (German Published Specification) No. 2,844,270.

In detail, process ($b_2$) is carried out, for example for the preparation of 5-chloromethyl-2,4-dichlorothiazole, by a procedure in which 2,4-dichloro-5-methylthiazole is reacted with chlorine with exposure to light, in particular in the presence of UV light, by vaporizing the 2,4-dichloro-5-methylthiazole in a vaporizing vessel surmounted by a tube designed as a condenser in the upper section and as a column in the lower section and in the centre of which is the reaction space, condensing the vapour in the condenser, so that the condensate drips onto a device let into the reaction space and reacts there with the chlorine introduced through the device to give 5-chloromethyl-2,4dichlorothiazole, which is flushed by the condensate dripping from the condenser into the vaporisation vessel through a tube let into the column.

Process (b₂) is preferably carried out at the boiling point of 2,4-dichloro-5-methylthiazole (about 200° to 210° C.) and without a diluent.

The effect of the special apparatus, the functioning of which is described in detail in DE-OS (German Published Specification) No. 2,844,270 is that, for example, 5-chloromethyl-2,4-dichlorothiazdle (Ib) containing only small amounts of products with a higher degree of chlorination is formed in high selectivity from 2,4-dichloro-5-methylthiazole (Ia). The formation of products with a higher degree of chlorination can also be suppressed by, for example, chlorinating the 2,4-dichloro-5-methylthiazole only to a conversion of, for example, 70 to 90% instead of to a conversion of 100%.

For variants (β) and (γ) of chlorination process (b), the same comments apply in the general sense as for variant (α). The compounds with a moderate degree of chlorination (Ib and Ic) can of course be converted individually or as mixtures into compounds with a higher degree of chlorination (Ic and Id).

The compounds of the formula (I) are useful starting substances for the preparation of highly active herbicides. For this, one or more chlorine atoms are initially replaced by fluorine, for example

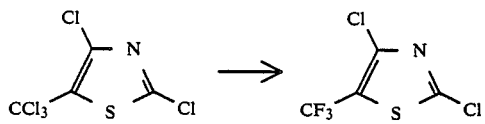

and the fluorine compounds thus obtained are reacted with hydroxyacetic acid amides to give the substituted thiazol2-yl-oxyacetamides of high herbicidal activity, for example

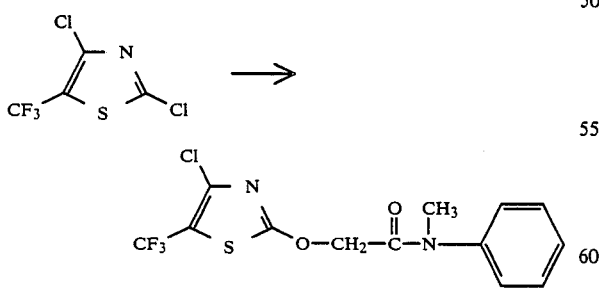

( see, for example, DE-OS (German Published Specification) No. 2,914,003, DE-OS (German Published Specification) No. 3,004,326 and European Pat. No. A-18,497, and the examples section).

The compounds of the formula (I) moreover themselves have a fungicidal action, in particular against *Piricularia oryzae* and against *Xanthomonas oryzae* in rice.

(A) PREPARATION EXAMPLES OF COMPOUNDS OF THE FORMULA (I)

EXAMPLE A-1

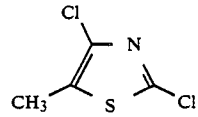

A mixture of 750 ml of phosphorus oxychloride, 157.2 g (1.2 moles) of 5-methyl-2,4-thiazolidinedione and 4 ml of dimethylformamide was heated under reflux, with stirring, until the evolution of gas had virtually ended (about 6 hours). The cooled reaction mixture was then poured in portions onto 5 kg of ice, while stirring thoroughly. The mixture was then extracted by shaking three times with about one liter of methylene chloride each time, the methylene chloride was stripped off in a rotary evaporator (Rotavapor) and the residue (187.3 g) was distilled. 159.1 g (corresponding to 78.9% of theory) of 2,4-dichloro-5-methylthiazole with a purity, determined by gas chromatography, of 99.9% were obtained at 86° C./18 mbar. Boiling point under atmospheric pressure: 203° C.

EXAMPLE A-2

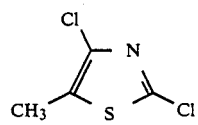

The procedure followed was analogous to Example 1, with the difference that instead of 4 ml, only 2 ml of dimethylformamide were employed. The yield of pure 2,4-dichloro-5-methylthiazole was 74.8% of theory.

EXAMPLE A-3

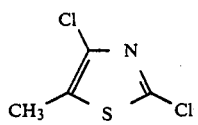

The procedure followed was analogous to Example 1, with the difference that instead of 4 ml only 2 ml of dimethylformamide and instead of 750 ml only 375 ml of phosphorus oxychloride were reacted. The yield of pure 2,4-dichloro-5-methylthiazole was 66.6% of theory.

EXAMPLE A-4

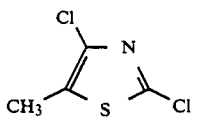

The procedure followed was initially analogous to Example 1. When the evolution of gas had ended, all the distillable constituents were distilled off under a water-pump vacuum from the reaction mixture at about 20 to 86° C./18 mbar up to a heating bath temperature of about 150° C. Most of the phosphorus oxychloride recovered was then distilled off over a column under atmospheric pressure at about 106° C. The residue was stirred in 2 l of ice-water, the aqueous phase, after hydrolysis of the residual amounts of phosphorus oxychloride, was extracted three times by shaking with one litre of methylene chloride each time, the methylene chloride was stripped off in a Rotavapor and the residue (152.4 g) was distilled. 147.7 g (corresponding to 73.3% of theory) of 2,4-dichloro-5-methylthiazole, which was pure according to gas chromatography, were obtained at 83° to 85° C./16 mbar.

EXAMPLE A-5

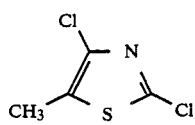

A mixture of 3 liters of phosphorus oxychloride, 630 g (4.81 moles) of 5-methyl-2,4-thiazolidinedione and 16 ml of dimethylformamide was heated under reflux, with stirring, until the evolution of gas had virtually ended (about 8 hours). All the distillable contents of the reaction mixture were then distilled off under a waterpump vacuum up to a heating bath temperature of about 180° C. According to analysis by gas chromatography, the distillate consisted to the extent of 99.7% of phosphorus oxychloride and of 2,4-dichloro-5-methylthiazole. The content of 2,4-dichloro-5-methylthiazole determined by gas chromatography, was 595.7 g (corresponding to 73.7% of theory). Subsequent fractional distillation on a column with a reflux separator gave pure 2,4-dichloro-5-methylthiazole at 86° C./18 mbar.

EXAMPLE A-6

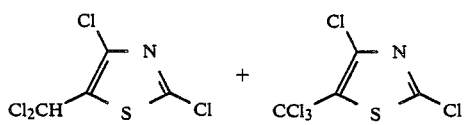

1,690 g (23.8 moles) of chlorine were passed into a mixture of 336 g (2 moles) of 2,4-dichloro-5-methylthiazole and 350 ml of carbon tetrachloride, in the course of 15 hours, in a cylindrical vessel equipped with a thermometer, reflux condenser, laboratory immersion lamp (Hg high-pressure lamp, Hanau) and, at the bottom, a glass frit for inlet of gas. In the first 10 hours of the chlorination period, the bottom temperature was 80° to 85° C.; in the last 5 hours, the temperature rose (by evaporation losses of CCl4) up to about 120° C.

According to gas chromatography, the reaction mixture consisted to the extent of 39.1% of 5-dichloromethyl-2,4-dichlorothiazole and to the extent of 53.5% of 5-trichloromethyl-2,4-dichlorothiazole. The remainder consisted of undesirable by-products with a higher chlorine content. For distillative working up, see the next example No. 7.

EXAMPLE A-7

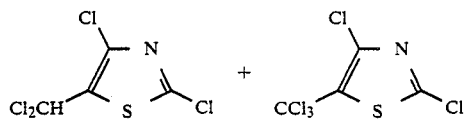

5,170 g (72.8 moles) of chlorine were passed, into a mixture of 1,008 g (6 moles) of 2,4-dichloro-5-methylthiazole and 1,050 ml of carbon tetrachloride, in the course of about 62 hours, in an apparatus analogous to Example 6 at a bath temperature of 100° C. and a bottom temperature of between 80° and 100° C.

According to gas chromatography, the reaction mixture consisted to the extent of 28.8% of 5-dichloromethyl-2,4-dichlorothiazole and to the extent of 64.7% of 5-trichloromethyl-2,4-dichlorothiazole. The remainder consisted of undesirable by-products with a higher chlorine content. Working-up by distillation was carried out together with the product mixture from the previous example No. 6. For this, a packed column (contents: Wilson glass spirals 3 to 4 mm in diameter) which had a mirrored vacuum jacket and an effective length of 1 m and was equipped with a column head with a magnetic vapour separator (reflux ratio 80:2) was used.

538 g (27.9%) of 5-dichloromethyl-2,4-dichlorothiazole (purity according to gas chromatography: 98.3%) were obtained at 120° to 121° C./20 mbar and 1,301 g (58.6%) of 5-trichloromethyl-2,4-dichlorothiazole (purity according to gas chromatography: 97.8%) were obtained at 136° to 137° C./19 mbar.

EXAMPLE A-8

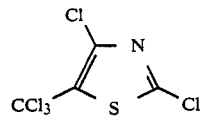

340 g of chlorine were passed into 1,008 g (6 moles) of 2,4-dichloro-5-methylthiazole at 200° to 210° C. in the course of 6 hours in an apparatus analogous to Example 6, and a further 860 g of chlorine (1,200 g=16.9 moles in total) were then passed in at between 210° and 240° C. in the course of 7 hours. The gas chromatogram of the crude mixture showed that of the four possible 2,4-dichlorothiazoles (Ia) to (Id), only 2,4-dichloro-5-(trichloromethyl)-thiazole (Id) was present. Working-up by distillation gave 773 g (49.1%, based on the amount of chlorine employed) of 2,4-dichloro-5-(trichloromethyl)-thiazole at 136° to 137° C./19mbar. Purity according to gas chromatography: 97.1%.

EXAMPLE A-9

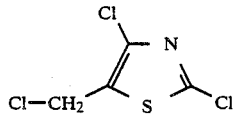

205 g (1.22 moles) of 2,4-dichloro-5-methylthiazole were chlorinated in an apparatus described on pages 18 and 23 of DT-OS (German Published Specification) No. 2,844,270, under UV irradiation with an Hg high pressure lamp and while boiling (bottom temperature initially 205° C.) As soon as the bottom temperature had reached 235° C., the chlorination was interrupted: conversion about 80%. According to analysis by gas chromatography, the chlorination mixture had the following composition: 19.5% of 2,4-dichloro-5-methylthiazole, 79.0% of 5-chloromethyl-2,4-dichlorothiazole and 1.5% of 2,4-dichloro-5-(dichloromethyl)-thiazole.

Fractional distillation on a packed column which had an effective length of 30 cm and was fitted with glass rings 2 mm in diameter and 2 mm in length gave 145 g (72%, based on the conversion) of 5-chloromethyl-2,4-dichlorothiazole at a boiling point of 118°–119° C./20 mbar; $n_D^{20} = 1.5835$; purity according to gas chromatography: 98.5%.

EXAMPLE A-10

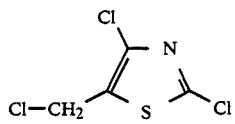

100 g (1.41 moles) of chlorine were passed into a mixture of 117.5 g (0.7 mole) of 2,4-dichloro-5-methylthiazole and 400 ml of carbon tetrachloride at the reflux temperature (about 82° C.) in the course of 8 hours, in a three-necked flask equipped with a stirrer, thermometer, reflux condenser and gas inlet tube. A neon daylight tube (fume cupboard illumination) at a distance of about 80 cm was used as the light source. According to analysis by gas chromatography (elimination of carbon tetrachloride), the chlorination mixture had the following composition: 16.0% of 2,4-dichloro-5-methylthiazole, 73.6% of 5-chloromethyl-2,4-dichlorothiazole and 10.0% of 2,4-dichloro-5-(dichloromethyl)-thiazole.

EXAMPLE A-11

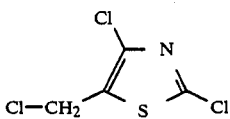

Chlorine was passed into a mixture of 78.9 g (0.47 mole) of 2,4-dichloro-5-methylthiazole and 200 ml of carbon tetrachloride at the reflux temperature in the course of 6 hours in an apparatus analogous to Example 10. Diffuse daylight (cloudy sky, distance from window about 5 m) was used as the sole source of light. According to analysis by gas chromatography, the chlorination mixture had the following composition: 89.3% of 2,4-dichloro-5-methylthiazole, 9.6% of 5-chloromethyl-2,4-dichlorothiazole and 1.0% of 2,4-dichloro-5-(dichloromethyl)-thiazole.

EXAMPLE A-12

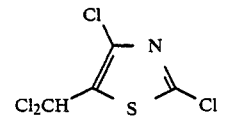

100 g (1.41 moles) of chlorine were passed into a mixture of 59 g (0.35 mole) of 2,4-dichloro-5-methylthiazole and 450 ml of carbon tetrachloride at the reflux temperature (about 80° C.) in the course of 6 hours in an apparatus analogous to Example 6.

According to gas chromatography, the reaction mixture consisted of: 2.0% of 5-chloromethyl-2,4-dichlorothiazole, 9.4% of 2,4-dichloro-5-(dichloromethyl)-thiazole and 7.9% of 2,4-dichloro-5-(trichloromethyl)-thiazole.

Fractional distillation on a packed column about 30 cm in length gave 48.5 g of 2,4-dichloro-5-(dichloromethyl)-thiazole in a purity, according to gas chromatography, of 94.0% as the main fraction at a boiling point of 122°–125° C./20 mbar. Yield (based on 100% pure product): 54 of theory.

EXAMPLE A-13

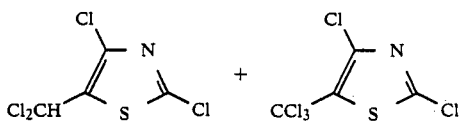

1,000 g (14.1 moles) of chlorine were passed into a mixture of 336 g (2 moles) of 2,4-dichloro-5-methylthiazole and 500 ml of carbon tetrachloride at the reflux temperature (about 80° C.) in the course of 10 hours in an apparatus analogous to Example A-8. According to gas chromatography, the reaction mixture consisted to the extent of 71.6% of 2,4-dichloro-5-(dichloromethyl)-thiazole, to the extent of 24.5% of 2,4-dichloro-5-(trichloromethyl)-thiazole and to the extent of 2.2% of undesirable by-products with a higher chlorine content.

EXAMPLE A-14

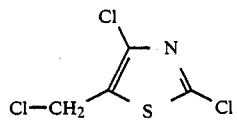

140 g (1.97 moles) of chlorine were passed into a mixture of 336 g (2 moles) of 2,4-dichloro-5-methylthiazole and 500 ml of carbon tetrachloride, at the reflux temperature (about 85° C.) in the course of 4.5 hours, in a three-necked flask equipped with a stirrer, thermometer, reflux condenser and gas inlet tube. A neon daylight tube (fume cupboard illumination) at a distance of about 80 cm was used as the light source. According to analysis by gas chromatography (elimination of carbon tetrachloride), the chlorination mixture had the following composition: 91.4% of 2,4-dichloro-5-methylthiazole, 8.5% of 5-chloromethyl-2,4-dichlorothiazole and 0.1% of 2,4-dichloro-5-(dichloromethyl)-thiazole.

EXAMPLE A-15

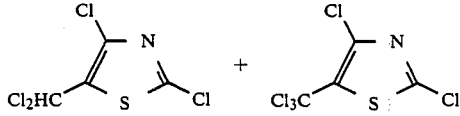

4,290 g (60.4 moles) of chlorine were passed into 2,167 g of a mixture of 72.4% of 2,4-dichloro-5-methylthiazole, 9.1% of 5-chloromethyl-2,4-dichlorothiazole and 18.4% of 2,4-dichloro-5-dichloromethylthiazole at an internal temperature of 140° to 16° C. in the course of 12 hours in an apparatus analogous to Example 6. The gas chromatogram of the crude mixture showed the following composition: 18.1% of 2,4-dichloro-5-dichloromethylthiazole and 80.9% of 2,4-dichloro-5-trichloromethylthiazole.

(B) PREPARATION EXAMPLES FOR FLUORINE-CONTAINING INTERMEDIATE PRODUCTS products

EXAMPLE 1

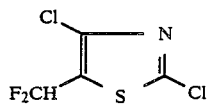

430 g (1.8 moles) of 2,4-dichloro-5-dichloromethyl1,3-thiazole are fluorinated with 650 ml of anhydrous hydrofluoric acid in a VA autoclave at 137°–140° C./18–22 bar. The hydrogen chloride formed is let down continuously. At the end of the reaction, the excess hydrofluoric acid is stripped off in vacuo at room temperature, the residue is poured onto ice-water and the mixture is taken up in methylene chloride, dried over sodium sulphate and distilled.

275 g (74.3% of theory) of 2,4-dichloro-5-difluoromethyl-1,3-thiazole, boiling point 12 mbar/6-5°–66°$n_D^{20}$=1.5070; and 30 g of constituents with a higher degree of fluorination are obtained.

EXAMPLES B-2 and B-3

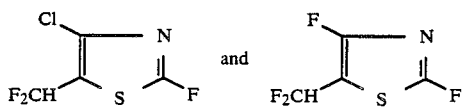

230 g (1.12 moles) of 2,4-dichloro-5-difluoromethyl-1,3-thiazole are stirred with 131 g (2.25 moles) of potassium fluoride in 339 ml of tetramethylene sulphone at 160° C. for 3 hours. The fluorinated product is then distilled off in vacuo up to the boiling point of the tetramethylene sulphone.

Redistillation gives: 76 g (40% of theory) of 2,4-difluoro-5-difluoromethyl-1,3-thiazole of boiling point bp: 108°–9° C.; refractive index $n_D^{20}$=1.408; and 47 g (22.4% of theory) of 2-fluoro-4-chloro-5-difluoromethyl-1,3-thiazole of boiling point bp: 141°–3° C.; refractive index $n_D^{20}$=1.4528; as well as 40 g of starting compound.

EXAMPLES B-4 and B-5

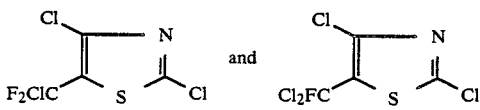

227 g (0.836 mole) of 2,4-dichloro-5-trichloromethyl-1,3-thiazole are fluorinated with 200 ml of anhydrous hydrofluoric acid in a VA autoclave at 50° C./3–8 bar. The hydrogen chloride formed is let down continuously. At the end of the reaction (about 4 hours), the mixture is cooled to room temperature and the excess hydrofluoric acid is stripped off in vacuo down to 100 mbar. The residue is poured onto ice-water and the mixture is taken up in methylene chloride, dried over sodium sulphate and distilled.

This gives: 84 g (39.5% of theory) of 2,4-dichloro-5-difluoro-chloromethyl-1,3-thiazole of boiling point bp: 76°–8° C./18 mbar, refractive index $n_D^{20}$=1.5120; and 67 g (33.7% of theory) of 2,4-dichloro-5-dichlorofluoromethyl-1,3-thiazole of boiling point bp: 105°–107° C./18 mbar, refractive index $n_D^{20}D$=1.5539; as well as 12 g of starting compound.

If the reaction is carried out at 60° C./5 bar, 2,4-dichloro-5-difluorochloromethyl-1,3-thiazole is obtained in a yield of 71% of theory.

EXAMPLE B-6

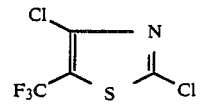

500 g (1.84 moles) of 2,4-dichloro-5-trichloromethyl-1,3-thiazole are fluorinated with 40 ml of anhydrous hydrofluoric acid in a VA autoclave at 120°–140° C./25–20 bar for 3 hours. The hydrogen chloride formed is let down continuously. At the end of the reaction, the mixture is cooled and the excess hydrofluoric acid is stripped off under a waterpump vacuum down to 100 mbar. The residue is poured onto ice-water and the mixture is taken up in methylene chloride, dried over sodium sulphate and distilled.

This gives: 280 g (68.5% of theory) of 2,4-dichloro-5-trifluoromethyl-1,3-thiazole of boiling point bp: 50° C./16 mbar; refractive index $n_D^{20}$=of partially fluorinated compounds.

(C) Preparation examples for herbicidally active thiazol-2-yl-oxyacetamides

EXAMPLE C-1

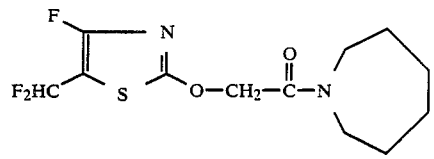

8.5 g (0.05 mole) of 2-chloro-4-fluoro-5-difluoromethyl-1,3-thiazole in 10 ml of acetonitrile are slowly added dropwise to 7.9 g(0.05 mole) of hydroxyacetic acid N,N-hexamethyleneamide and 3.1 g (0.05 mole) of potassium hydroxide in 100 ml of isopropanol at −20° C., with stirring, and, when the addition has ended, the mixture is stirred at −20° C. for a further 12 hours. When the starting substance can no longer be detected in the thin layer chromatogram, the reaction mixture is poured into water and the crystalline product is filtered off with suction and rinsed with water and a little cold ligroin. 12 g (80% of theory) of 2-(4-fluoro-5-difluoromethylthiazol-2-yloxy)-acetic acid N,N-hexamethyleneamide of melting point 66° C. are obtained.

The following compounds of the following general formula are obtained in a corresponding manner - compare Table 1:

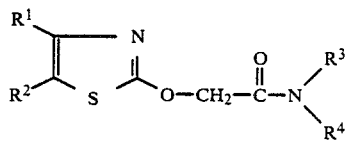

(Where the substances are obtained as oils, they are isolated from the aqueous mixture by extraction with an organic solvent, as is generally customary).

TABLE 1

| Example No. | R¹ | R² | −N(R³)(R⁴) | Physical data |
|---|---|---|---|---|
| C-2 | Cl | CH$_3$ | hexamethyleneimino (azepan-1-yl) | M.p.: 61° C. |
| C-3 | Cl | CH$_3$ | N(C$_2$H$_5$)$_2$ | M.p.: 42° C. |
| C-4 | Cl | CH$_3$ | N(CH$_3$)(C$_6$H$_5$) | M.p.: 82° C. |
| C-5 | Cl | CHCl$_2$ | N(CH$_3$)(C$_6$H$_5$) | M.p.: 94° C. |
| C-6 | Cl | CF$_2$Cl | N(CH$_3$)(C$_6$H$_5$) | M.p.: 84° C. |
| C-7 | Cl | CF$_2$Cl | N(C$_2$H$_5$)$_2$ | $n_D^{20}$ = 1.5060 |
| C-8 | Cl | CF$_2$Cl | N(OCH$_3$)(CH(CH$_3$)C$_2$H$_5$) | $n_D^{20}$ = 1.4950 |
| C-9 | Cl | CHF$_2$ | N(O—CH$_2$CH$_2$OC$_2$H$_5$)(CH(CH$_3$)$_2$) | $n_D^{20}$ = 1.4891 |
| C-10 | Cl | CHF$_2$ | N(C$_2$H$_5$)$_2$ | M.p.: 64° C. |
| C-11 | Cl | CHF$_2$ | hexamethyleneimino | M.p.: 72° C. |
| C-12 | Cl | CHF$_2$ | N(CH$_3$)(C$_6$H$_5$) | M.p.: 78° C. |
| C-13 | F | CHF$_2$ | N(C$_2$H$_5$)$_2$ | M.p.: 50° C. |
| C-14 | Cl | CHF$_2$ | N(CH$_3$)(C$_6$H$_5$) | M.p.: 74° C. |
| C-15 | Cl | CF$_3$ | N(CH$_3$)(C$_6$H$_5$) | M.p.: 115° C. |
| C-16 | Cl | CF$_3$ | hexamethyleneimino | M.p.: 70° C. |
| C-17 | Cl | CF$_3$ | N(C$_2$H$_5$)$_2$ | M.p.: 39° C. |
| C-18 | Cl | CF$_3$ | N(CH$_2$CH=CH$_2$)$_2$ | M.p.: 66° C. |
| C-19 | Cl | CF$_3$ | N(CH$_3$)$_2$ | M.p.: 58° C. |
| C-20 | Cl | CF$_3$ | 4-methylpiperidin-1-yl | M.p.: 72° C. |
| C-21 | Cl | CF$_3$ | 3-methylpiperidin-1-yl | $n_D^{20}$ = 1.4908 |
| C-22 | Cl | CF$_3$ | 3,5-dimethylpiperidin-1-yl | $n_D^{20}$ = 1.4965 |
| C-23 | Cl | CF$_3$ | N((CH$_2$)$_2$—CH$_3$)$_2$ | $n_D^{20}$ = 1.4774 |
| C-24 | Cl | CF$_3$ | N(OCH$_3$)(CH(CH$_3$)C$_2$H$_5$) | $n_D^{20}$ = 1.4715 |

TABLE 1-continued

| Example No. | $R^1$ | $R^2$ | 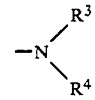  | Physical data |
|---|---|---|---|---|
| C-25 | Cl | $CF_3$ | 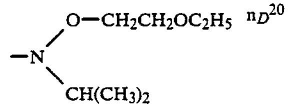  | $n_D^{20} = 1.5664$ |
| C-26 | F | $CHF_2$ | 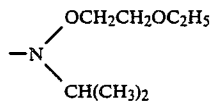  | M.p.: 54–56° C. |
| C-27 | F | $CHF_2$ | 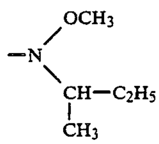  | $n_D^{20} = 1.4715$ |

USE EXAMPLES

EXAMPLE I

Pre-emergence test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentraticn of the active compound in the preparation is of no importance, only the amount of active compound applied per unit area being decisive. After three weeks, the degree of damage to the plants is rated in % damage in comparison to the development of the untreated control. The figures denote:

0%=no action (like untreated control)

100%=total destruction

In this test, a clearly superior herbicidal activity compared with the prior art, with a comparable selectivity towards useful plants, is shown, for example, by the compounds according to the following preparation examples: C-12, C-15, C-16, C-17 and C-24.

EXAMPLE II

*Xanthomonas oryzae* test/bacteriosis/rice systemic

Solvent: 122.5 parts by weight of dimethylformamide

Emulsifier: 2.5 parts by weight of alkylaryl polyglycol ether

To produce a suitable preparation of active compound, 1 part by weight of active compound is mixed with the stated amount of solvent and emulsifier, and the concentrate is diluted with water to the desired concentration.

To test for systemic properties, standard soil in which young plants have been grown is watered with 100 ml of the preparation of active compound. 3 days after the treatment, the plants are inoculated with an aqueous suspension of *Xanthomonas oryzae* by pricking. Thereafter, the plants remain in a greenhouse at 24° to 26° C. and 70 to 80% relative atmospheric humidity for 10 to 14 days until they are evaluated.

In this test, for example, compound (1c) exhibits a clear biological action.

TABLE A

Xanthomonas oryzae test/bacteriosis/rice systemic

| Active compounds | Amount applied in mg of active compound per 100 $cm^2$ | Disease infestation in % of the untreated controls, systemic |
|---|---|---|
|  (Ic) | 10 | 20 |

What is claimed is:

1. A 2,4-dichlorothiazole derivatives of the formula 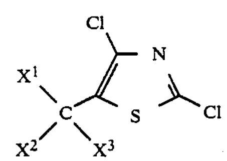 in which $X^1$ represents chlorine, $X^2$ represents hydrogen or chlorine and $X^3$ represents hydrogen or chlorine.

2. A 2,4-dichlorothiazole derivatives according to claim 1, wherein said derivative is selected from the group consisting of 2,4-dichloro-5-chloromethyl-thiazole, 2,4-dichloro-5-dichloromethyl-thiazole and 2,4-dichloro-5-trichloromethyl-thiazole.

3. A fungicidal composition containing as active ingredient a fungicidally effective amount of a compound according to claim 1 in admixture with a diluent.

4. A method of combating fungi which comprises applying to the fungi or to a habitat thereof a fungicidally effective amount of a compound according to claim 1.

* * * * *

UNITED STATES PATENT AND TRADEMARK OFFICE
CERTIFICATE OF CORRECTION

PATENT NO. : 4,788,208
DATED : Nov. 29, 1988
INVENTOR(S) : Beck et al.

It is certified that error appears in the above-identified patent and that said Letters Patent is hereby corrected as shown below:

| | |
|---|---|
| Col. 5, line 21 | Correct spelling of --dichlorothiazole-- |
| Col. 5, line 48 | Insert -- - -- before "2" |
| Col. 10, line 5 | Insert --8-- before "9.4" |
| Col. 10, line 13 | Insert --.8%-- after "54" |
| Col. 11, line 7 | Delete "products" in second instance |
| Col. 11, line 9 | Insert --B-- after "Example" |
| Col. 11, line 17 | Insert -- - -- before "1" |
| Col. 11, line 27 | Insert --C;-- after "66°" |
| Col. 12, line 4 | Delete "D" after "20" |
| Col. 12, line 18 | Insert --7-- before "40" |
| Col. 12, line 29 | Insert --1.4710; as well as 63g-- after "=" |
| Col. 16, line 34 | Delete "derivatives" and substitute --derivative-- |
| Col. 16, line 47 | Delete "derivatives" and substitute --derivative-- |
| Title Page, under "Inventors, line 2 | Delete "Schubart" and substitute --Schubert--. |

Signed and Sealed this

Twenty-first Day of November, 1989

Attest:

JEFFREY M. SAMUELS

Attesting Officer     Acting Commissioner of Patents and Trademarks